United States Patent [19]

Andoh et al.

[11] Patent Number: 5,733,935

[45] Date of Patent: Mar. 31, 1998

[54] HYDROXYLAMINE DERIVATIVES AND FUNGICIDES CONTAINING THE SAME

[75] Inventors: Nobuharu Andoh, Osaka; Tsutomu Nishiguchi; Katsutoshi Endo, both of Kawachinagano, all of Japan

[73] Assignee: Nihon Nohyaku Co., Ltd., Tokyo, Japan

[21] Appl. No.: 665,291

[22] Filed: Jun. 17, 1996

[30] Foreign Application Priority Data

Jun. 29, 1995 [JP] Japan ..................... 7-186463

[51] Int. Cl.[6] ............... A61K 31/16; A61K 31/18; A61K 31/27; A61K 31/15

[52] U.S. Cl. ............ 514/640; 514/354; 514/355; 514/448; 514/471; 514/478; 514/479; 514/485; 514/486; 514/489; 514/490; 514/601; 514/602; 514/604; 514/605; 514/617; 514/618; 514/619; 514/620; 514/622; 514/625; 514/626; 514/627; 514/628; 514/629; 514/630; 564/84; 564/90; 564/92; 564/98; 564/99; 564/162; 564/166; 564/170; 564/171; 564/176; 564/177; 564/179; 564/197; 564/201; 564/204; 564/209; 564/215; 564/218; 564/223; 564/256; 564/257; 560/24; 560/29; 560/30; 560/31; 560/148; 560/156; 560/157; 560/159; 560/160; 560/161; 546/316; 546/323; 549/72; 549/487

[58] Field of Search .................. 514/617, 618, 514/619, 620, 622, 625, 626, 627, 628, 629, 630, 354, 355, 448, 471, 478, 479, 485, 486, 489, 490, 601, 602, 604, 605, 640; 564/162, 166, 170, 171, 176, 177, 179, 197, 201, 204, 209, 215, 218, 223, 84, 90, 92, 98, 99, 256, 257; 546/316, 323; 549/72, 487; 560/24, 29, 30, 31, 148, 156, 157, 159, 160, 161

[56] References Cited

U.S. PATENT DOCUMENTS 3,133,963  5/1964  Horrom ..................... 564/176
4,661,632  4/1987  Oecki et al. ............... 564/217
4,946,865  8/1990  Takahashi et al. ......... 514/467

*Primary Examiner*—Peter O'Sullivan
*Attorney, Agent, or Firm*—Oliff & Berridge, PLC

[57] ABSTRACT

A hydroxylamine derivatives of formula (I):

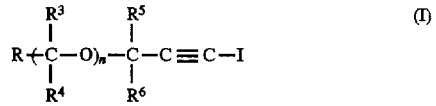

wherein R represents

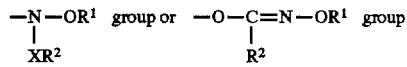

in which $R^1$ and $R^2$ represents alkyl group, alkenyl group, alkynyl group, cycloalkyl group, haloalkyl group, haloalkynyl group, alkoxy - alkyl group, phenoxy - alkyl group, alkylthio - alkyl group, alkylsulfonyl - alkyl group, alkylamino - alkyl group, phenyl group, benzyl group, phenethyl group, cinnamyl group, pyridyl group, furyl group, thienyl group, X represents $CO_2$, CO or $SO_2$, and $R^3$, $R^4$, $R^5$ and $R^6$ represent a hydrogen atom or a lower alkyl group, and n represents 0 or 1, and fungicides contain said compound as an active ingredient.

The compounds of the present invention have excellent effects for controlling wood-rot fungi, plant diseases and fungi of humans and animals, and are useful as industrial, agricultural and medical fungicides.

6 Claims, No Drawings

HYDROXYLAMINE DERIVATIVES AND FUNGICIDES CONTAINING THE SAME

BACKGROUND OF THE INVENTION

1. Field of the Invention

The present invention relates to hydroxylamine derivatives represented by formula (I)

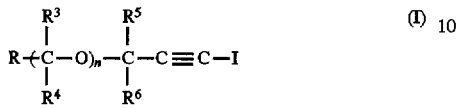

wherein R represents

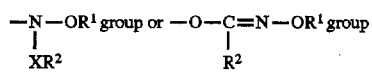

in which $R^1$ and $R^2$ are the same or different and each represents a $C_1$–$C_{12}$ alkyl group; a $C_2$–$C_7$ alkenyl group; a $C_2$–$C_7$ alkynyl group; a $C_3$–$C_7$ cycloalkyl group; a $C_1$–$C_7$ haloalkyl group; a $C_2$–$C_7$ haloalkynyl group; a $C_1$–$C_7$ alkoxy-$C_1$–$C_7$ alkyl group; a phenoxy $C_1$–$C_7$-alkyl group; a phenoxy $C_1$–$C_7$-alkyl group substituted on the ring by one to five substituents which are the same or different and which are selected from a halogen atom, a nitro group, a cyano group, a $C_1$–$C_7$ alkyl group, a $C_1$–$C_7$ haloalkyl group, a $C_1$–$C_7$ alkoxy group, a $C_1$–$C_7$ haloalkoxy group, a $C_1$–$C_7$ alkoxycarbonyl group, a $C_1$–$C_7$ alkylthio group, a $C_1$–$C_7$ haloalkylthio group, a $C_1$–$C_7$ alkylsulfonyl group, a $C_1$–$C_7$ haloalkylsulfonyl group and an amino group substituted by one or two $C_1$–$C_7$ alkyl groups which are the same or different; a $C_1$–$C_7$ alkylthio-$C_1$–$C_7$ alkyl group; a $C_1$–$C_7$ alkylsulfonyl-$C_1$–$C_7$ alkyl group; an amino-$C_1$–$C_7$ alkyl group substituted by one or two substituents which are the same or different and which are selected from a $C_1$–$C_7$ alkyl group and a $C_3$–$C_7$ cycloalkyl group; a phenyl group; a phenyl group substituted on the ring by one to five substituents which are the same or different and which are selected from a halogen atom, a nitro group, a cyano group, a $C_1$–$C_7$ alkyl group, a $C_1$–$C_7$ haloalkyl group, a $C_1$–$C_7$ alkoxy group, a $C_1$–$C_7$ haloalkoxy group, a $C_1$–$C_7$ alkoxycarbonyl group, a $C_1$–$C_7$ alkylthio group, a $C_1$–$C_7$ haloalkylthio group, a $C_1$–$C_7$ alkylsulfonyl group, a $C_1$–$C_7$ haloalkylsulfonyl group and an amino group substituted by one or two $C_1$–$C_7$ alkyl groups which are the same or different; a benzyl group; a benzyl group substituted on the ring by one to five substituents which are the same or different and which are selected from a halogen atom, a nitro group, a cyano group, a $C_1$–$C_7$ alkyl group, a $C_1$–$C_7$ haloalkyl group, a $C_1$–$C_7$ alkoxy group, a $C_1$–$C_7$ haloalkoxy group, a $C_1$–$C_7$ alkoxycarbonyl group, a $C_1$–$C_7$ alkylthio group, a $C_1$–$C_7$ haloalkylthio group, a $C_1$–$C_7$ alkylsulfonyl group, a $C_1$–$C_7$ haloalkylsulfonyl group and an amino group substituted by one or two $C_1$–$C_7$ alkyl groups which are the same or different; a naphthyl group; a naphthyl group substituted on the ring by from one to seven substituents which are the same or different and which are selected from a halogen atom, a nitro group, a cyano group, a $C_1$–$C_7$ alkyl group, a $C_1$–$C_7$ haloalkyl group, a $C_1$–$C_7$ alkoxy group, a $C_1$–$C_7$ haloalkoxy group, a $C_1$–$C_7$ alkoxycarbonyl group, a $C_1$–$C_7$ alkylthio group, a $C_1$–$C_7$ haloalkylthio group, a $C_1$–$C_7$ alkylsulfonyl group, a $C_1$–$C_7$ haloalkylsulfonyl group and an amino group substituted by one or two $C_1$–$C_7$ alkyl groups which are the same or different; a phenethyl group; a phenethyl group substituted on the ring by one to five substituents which are the same or different and which are selected from a halogen atom, a nitro group, a cyano group, a $C_1$–$C_7$ alkyl group, a $C_1$–$C_7$ haloalkyl group, a $C_1$–$C_7$ alkoxy group, a $C_1$–$C_7$ haloalkoxy group, a $C_1$–$C_7$ alkoxycarbonyl group, a $C_1$–$C_7$ alkylthio group, a $C_1$–$C_7$ haloalkylthio group, a $C_1$–$C_7$ alkylsulfonyl group, a $C_1$–$C_7$ haloalkylsulfonyl group and an amino group substituted by one or two $C_1$–$C_7$ alkyl groups which are the same or different; a cinnamyl group; a cinnamyl group substituted on the ring by one to five substituents which are the same or different and which are selected from a halogen atom, a nitro group, a cyano group, a $C_1$–$C_7$ alkyl group, a $C_1$–$C_7$ haloalkyl group, a $C_1$–$C_7$ alkoxy group, a $C_1$–$C_7$ haloalkoxy group, a $C_1$–$C_7$ alkoxycarbonyl group, a $C_1$–$C_7$ alkylthio group, a $C_1$–$C_7$ haloalkylthio group, a $C_1$–$C_7$ alkylsulfonyl group, a $C_1$–$C_7$ haloalkylsulfonyl group and an amino group substituted by one or two $C_1$–$C_7$ alkyl groups which are the same or different; a pyridyl group; a pyridyl group substituted on the ring by one to four substituents which are the same or different and which are selected from a halogen atom, a cyano group, a $C_1$–$C_7$ alkyl group, a $C_1$–$C_7$ haloalkyl group, a $C_1$–$C_7$ alkoxy group, a $C_1$–$C_7$ haloalkoxy group, a $C_1$–$C_7$ alkoxycarbonyl group, a $C_1$–$C_7$ alkylthio group, a $C_1$–$C_7$ haloalkylthio group, a $C_1$–$C_7$ alkylsulfonyl group, a $C_1$–$C_7$ haloalkylsulfonyl group and an amino group substituted by one or two $C_1$–$C_7$ alkyl groups which are the same or different; a furyl group; a furyl group substituted by one to three substituents which are the same or different and which are selected from a halogen atom, a nitro group, a cyano group and a $C_1$–$C_7$ alkyl group; a thienyl group; or a thienyl group substituted by one to three substituents which are the same or different and which are selected from a halogen atom, a nitro group, a cyano group, and a $C_1$–$C_7$ alkyl group, and X represents $CO_2$, CO or $SO_2$, $R^3$, $R^4$, $R^5$ and $R^6$ are the same or different and each represents a hydrogen atom or a $C_1$–$C_7$ alkyl group, and n represents 0 or an integer of 1, and a fungicide containing the same as an active ingredient.

2. Description of Prior Art

With respect to hydroxylamine derivatives, Japanese Patent Publication No. Sho 47-43,829 (JP-B-47 43829 (1972)) describes compounds represented by formula (A):

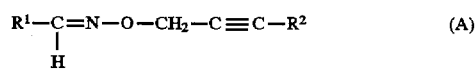

as an insecticide and an acaricide, and Japanese Patent Application Laid-Open No. Sho 55-36,498 (JP-A-55 36498 (1980)) describes compounds represented by formula (B):

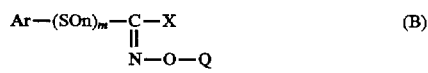

as a plant protective agent having activity against phytotoxicity of herbicides. However, it has not been known that these compounds exhibit fungicidal activity.

SUMMARY OF THE INVENTION

The present invention relates to novel hydroxylamine derivatives and a fungicide containing the same as an active ingredient.

The present inventors have conducted assiduous investigations to discover a novel fungicide, and have consequently found that hydroxylamine derivatives represented by the formula (I) in the present invention have strong fungicidal activity and are useful as an agricultural, industrial and medical fungicide. This finding has led to the completion of the present invention.

In the definitions for $R^1$ and $R^2$ in the formula (I), examples of the $C_1$–$C_{12}$ alkyl group include straight chain or branched alkyl groups having from 1 to 12 carbon atoms, such as methyl, ethyl, n-propyl, n-butyl, iso-butyl, sec-butyl, tert-butyl, n-pentyl, 1-ethyl-n-pentyl, n-hexyl, 2-ethyl-n-hexyl and n-decyl groups.

Examples of the $C_2$–$C_7$ alkenyl group include alkenyl groups having from 2 to 7 carbon atoms, such as vinyl, 1-propenyl, 2-propenyl, 1-methyl-2-propenyl, 1,1-dimethyl-2-propenyl, butenyl, pentenyl and hexenyl groups.

Examples of the $C_2$–$C_7$ alkynyl group include alkynyl groups having from 2 to 7 carbon atoms, such as ethynyl, 2-propynyl, 1-methyl-2-propynyl, 1,1-dimethyl-2-propynyl, butynyl, pentynyl and hexynyl.

Examples of the $C_3$–$C_7$ cycloalkyl group include cycloalkyl groups having from 3 to 7 carbon atoms, such as cyclopropyl, cyclobutyl, cyclopentyl and cyclohexyl groups.

Examples of the $C_1$–$C_7$ haloalkyl group include alkyl groups having from 1 to 7 carbon atoms and substituted with one or more halogen atoms which are the same or different, such as chloromethyl, bromomethyl, iodomethyl, fluoromethyl, difluoromethyl, trifluoromethyl, 1,1,1-trichloroethyl, 2,2,2-trifluoroethyl, 1,1,1,2,2-pentafluoroethyl, chloropropyl, fluorobutyl, chloropentyl and fluorohexyl groups.

Examples of the $C_2$–$C_7$ haloalkynyl group include alkynyl groups having from 2 to 7 carbon atoms and substituted by one or more halogen atoms which are the same or different, such as 3-chloro-2-propynyl, 3-fluoro-2-propynyl, 2-chloropropynyl, 2-fluoropropynyl, 4-chloro-2-butynyl and 4-fluoro-2-butynyl groups.

Examples of the $C_1$–$C_7$ alkoxy-$C_1$–$C_7$ alkyl group include alkoxy-alkyl groups such as methoxymethyl, methoxyethyl, ethoxymethyl, ethoxyethyl, methoxypropyl and ethoxybutyl groups.

Examples of the phenoxy-$C_1$–$C_7$ alkyl group include phenoxy-alkyl groups such as phenoxymethyl, phenoxyethyl, phenoxypropyl and phenoxybutyl groups.

Examples of the $C_1$–$C_7$ alkylthio-$C_1$–$C_7$ alkyl group include alkylthioalkyl groups such as methylthiomethyl, methylthioethyl, ethylthiomethyl, ethylthioethyl, methylthiopropyl and ethylthiobutyl groups.

Examples of the $C_1$–$C_7$ alkylsulfonyl-$C_1$–$C_7$ alkyl group include alkylsulfonylalkyl groups such as methylsulfonylmethyl, methylsulfonylethyl, ethylsulfonylmethyl, ethylsulfonylethyl, methylsulfonylpropyl and ethylsulfonylbutyl groups.

Examples of the aminoalkyl group having one or two substituents which are the same or different and which are selected from the alkyl group and the cycloalkyl group include amino alkyl groups such as methylaminomethyl, ethylaminomethyl, dimethylaminomethyl, diethylaminomethyl, dimethylaminoethyl, diethylaminomethyl, N-methyl-N-ethylaminomethyl, N-methyl-N-ethylaminoethyl, cyclopropylaminomethyl and cyclohexylaminoethyl groups.

Examples of the substituents of the substituted phenoxy $C_1$–$C_7$ alkyl group, the substituted phenyl group, the substituted naphthyl group, the substituted benzyl group, the substituted phenethyl group and the substituted cinnamyl group include the halogen atom, the nitro group, the cyano group, the $C_1$–$C_7$ alkyl group, the $C_1$–$C_7$ haloalkyl group, the $C_1$–$C_7$ alkoxy group, the $C_1$–$C_7$ haloalkoxy group, the $C_1$–$C_7$ alkoxycarbonyl group, the $C_1$–$C_7$ alkylthio group, the $C_1$–$C_7$ haloalkylthio group, the $C_1$–$C_7$ alkylsulfonyl group, the $C_1$–$C_7$ haloalkylsulfonyl group and the amino group having one or two substituents which are the same or different and which are selected from the $C_1$–$C_7$ alkyl group.

Examples of the substituents of the substituted pyridyl group include the halogen atom, the cyano group, the $C_1$–$C_7$ alkyl group, the $C_1$–$C_7$ haloalkyl group, the $C_1$–$C_7$ alkoxy group, the $C_1$–$C_7$ haloalkoxy group, the $C_1$–$C_7$ alkoxycarbonyl group, the $C_1$–$C_7$ alkylthio group, the $C_1$–$C_7$ haloalkylthio group, the $C_1$–$C_7$ alkylsulfonyl group, the $C_1$–$C_7$ haloalkylsulfonyl group and the amino group having one or two substituents which are the same or different and which are selected from the $C_1$–$C_7$ alkyl group.

Examples of the substituents of the substituted furyl group and the substituted thienyl group include the halogen atom, the nitro group, the cyano group and the $C_1$–$C_7$ alkyl group.

Examples of the $C_1$–$C_7$ alkyl group include alkyl groups having from 1 to 7 carbon atoms, such as methyl, ethyl, n-propyl, i-propyl, n-butyl, iso-butyl, sec-butyl, tert-butyl, n-pentyl and n-hexyl groups.

Examples of the $C_1$–$C_7$ haloalkyl group include alkyl groups having from 1 to 7 carbon atoms and having one or more substituents which are the same or different and which are selected from a halogen atom, such as chloromethyl, bromomethyl, iodomethyl, fluoromethyl, difluoromethyl, trifluoromethyl, chloromethyl, 1,1,1,2,2-pentafluoroethyl, chloropropyl and fluoropropyl groups.

Examples of the $C_1$–$C_7$ alkoxy group include alkoxy groups having from 1 to 7 carbon atoms, such as methoxy, ethoxy, n-propoxy, iso-propoxy, n-butoxy, iso-butoxy, tert-butoxy, n-pentyloxy and n-hexyloxy groups.

Examples of the $C_1$–$C_7$ haloalkoxy group include alkoxy groups having from 1 to 7 carbon atoms, such as chloromethoxy, fluoromethoxy, difluoromethoxy, trifluoromethoxy, 1-chloroethoxy, dichloroethoxy, chloropropoxy, fluoropropoxy, chlorobutoxy and fluorobutoxy groups.

Examples of the $C_1$–$C_7$ alkoxycarbonyl group include alkoxycarbonyl groups having from 1 to 7 carbon atoms, such as methoxycarbonyl, ethoxycarbonyl, n-propoxycarbonyl, i-propoxycarbonyl and n-butoxycarbonyl groups.

Examples of the $C_1$–$C_7$ alkylthio group include alkylthio groups having from 1 to 7 carbon atoms, such as methylthio, ethylthio, n-propylthio, iso-propylthio, n-butylthio, iso-butylthio, tert-butylthio, n-pentylthio and n-hexylthio groups.

Examples of the $C_1$–$C_7$ haloalkylthio group include alkylthio groups having from 1 to 7 carbon atoms and having one or more substituents which are the same or different and which are selected from a halogen atom, such as chloromethylthio, bromomethylthio, iodomethylthio, fluoromethylthio, difluoromethylthio, trifluoromethylthio, chloroethylthio, 1,1,1,2,2-pentafluoroethylthio, chloropropylthio and fluoropropylthio groups.

Examples of the $C_1$–$C_7$ alkylsulfonyl group include alkylsulfonyl groups having from 1 to 7 carbon atoms, such as methylsulfonyl, ethylsulfonyl, n-propylsulfonyl, i-propylsulfonyl, n-butylsulfonyl, iso-butylsulfonyl, secbutylsulfonyl, tert-butylsulfonyl, n-pentylsulfonyl and n-hexylsulfonyl groups.

Examples of the $C_1$–$C_7$ haloalkylsulfonyl group include alkylsulfonyl groups having from 1 to 7 carbon atoms and having one or more substituents which are the same or different and which are selected from a halogen atom, such as chloromethylsulfonyl, bromomethylsulfonyl, iodomethylsulfonyl, fluoromethylsulfonyl, difluoromethylsulfonyl, trifluoromethylsulfonyl, chloroethylsulfonyl, 1,1,1,2,2-pentafluoroethylsulfonyl, chloropropylsulfonyl and fluoropropylsulfonyl groups.

Examples of the amino group substituted by from one or two $C_1$–$C_7$ alkyl groups which are the same or different include amino groups such as methylamino, ethylamino, dimethylamino, diethylamino, dipropylamino, dibutylamino, N-methyl-N-ethylamino, and N-methyl-N-ethylamino groups.

Preferably, R represents

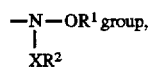

$R^1$ represents a methyl group, $R^2$ represents a $C_1$–$C_7$ alkyl group, a phenyl group, a substituted phenyl group having one or more substituents which are the same or different and which are selected from a halogen atom or a $C_1$–$C_7$ alkyl group, a benzyl group or a substituted benzyl group having one or more substituents which are the same or different and which are selected from a halogen atom or $C_1$–$C_7$ alkyl group, X represents CO or $CO_2$, $R^3$, $R^4$, $R^5$ and $R^6$ each represents a hydrogen atom, and n represents 0 or an integer of 1.

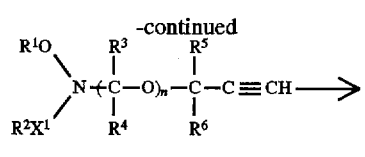

(IVa)

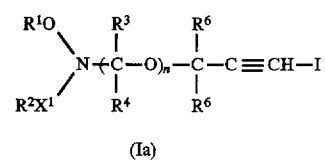

(Ia)

wherein $R^1$, $R^2$, $R^3$, $R^4$, $R^5$, $R^6$ and n have the same meanings as defined above, and $X^1$ represents $CO_2$ or $SO_2$, and hal represents a halogen atom.

That is, the compound of the formula (II) is treated with the compound of the formula (III) in an inert solvent in the presence of a base at a temperature of from room temperature to a reflux temperature to obtain a compound of formula (IVa). Then, the compound of the formula (IVa) is reacted in an inert solvent in the presence of a base and an iodination agent such as iodine, iodine monochloride, an iodine-morpholine complex or N-iodosuccinimide at a temperature of from approximately 0° C. to room temperature, whereby the hydroxylamine derivative of the formula (Ia) can be produced.

(2) When X is CO:

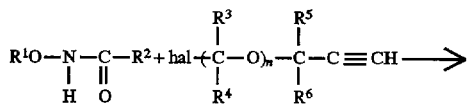

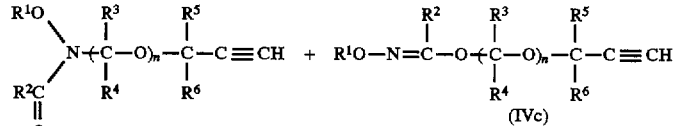

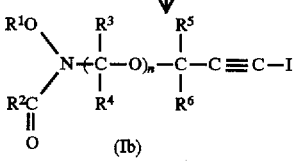

(Ib)

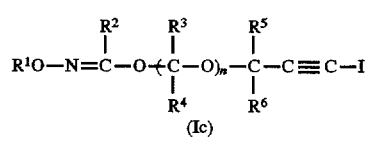

(Ic)

wherein $R^1$, $R^2$, $R^3$, $R^4$, $R^5$, $R^6$, n and hal have the same meanings as defined above.

That is, the mixture of the compounds of formulas (IVb) and (IVc) can be obtained by treating the compound of the formula (II') with the compound of the formula (III) in the presence of a base in a same manner as in (1). The compounds of the formulas (IVb) and (IVc) are separated through column chromatography or the like, and the iodination reaction is conducted as in (1), making it possible to produce hydroxylamine derivatives of the formulas (Ib) and (Ic).

(1) When X is $CO_2$ or $SO_2$:

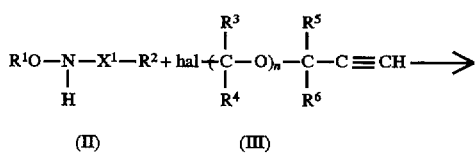

The compound of the formula (IVc) can be produced as schematically shown below.

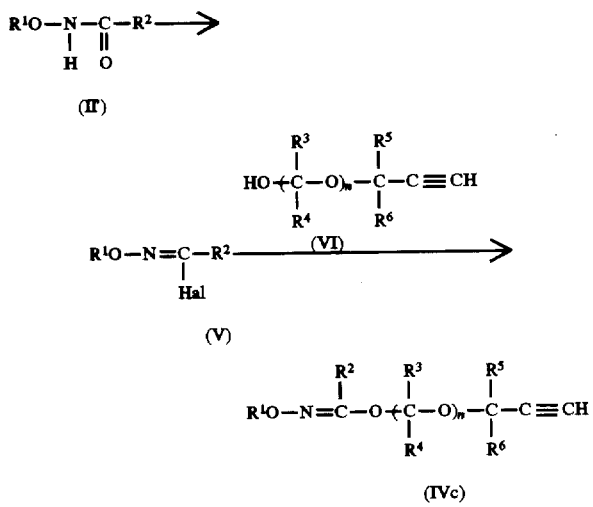

wherein $R^1$, $R^2$, $R^3$, $R^4$, $R^5$, $R^6$, n and hal have the same meanings as defined above.

That is, the compound of the formula (IVc) can be produced by reacting the compound of the formula (II') with a halogenation agent such as phosphorus pentachloride or the like and then reacting the resulting compound of the formula (V) with the compound of the formula (VI) in an inert solvent at a temperature of from room temperature to a reflux temperature of the inert solvent.

The base which is used in each reaction includes inorganic bases and organic bases. Appropriate examples thereof include sodium hydroxide, potassium hydroxide, potassium carbonate, sodium methoxide and sodium hydride. The base may be used in an amount which is an equimolar or more amount based on the compound of the formula (V).

Any inert solvent will do if it does not inhibit the reaction. Examples of the inert solvent include ketones such as acetone, methyl ethyl ketone and cyclohexanone; linear or cyclic ethers such as diethyl ether, diisopropyl ether, dimethoxyethane, tetrahydrofuran, dioxane, monoglyme and diglyme; esters such as methyl acetate and ethyl acetate; halogenated hydrocarbons such as dichloroethane, chloroform, carbon tetrachloride and tetrachloroethane; aromatic hydrocarbons such as benzene, chlorobenzene, nitrobenzene, toluene and xylene; nitriles such as acetonitrile; alcohols such as methanol, ethanol and isopropanol; dimethylformamide; dimethyl sulfoxide; water; and mixtures of thereof. When the two-phase reaction is conducted using water and a water-insoluble inert solvent, a phase transfer catalyst can be used. Examples of the phase transfer catalyst include triethylbenzylammonium chloride and trioctylmethylammonium chloride. Since each reaction is an equimolar reaction, it is preferable to use the reagent in an equimolar amount. However, the reagent in one reaction may be used in a larger amount.

The hydroxylamine derivatives of the formula (I) in the present invention are useful as agricultural, industrial and medical fungicides. As agricultural fungicides, the hydroxylamine derivatives are quite useful for controlling rice blast (*Pyricularia oryzae*) of a paddy, downy mildew (*Pseudoperonospora cubensis*) of a cucumber, late blight (*Phytophthora infestans*) of a tomato, brown spot (*Cladosporium cladosporioides*) of a grape, seedling blight (*Trichoderma viride*) of a paddy rice, alternaria brotch (*Alternaria mali*) of an apple, stem rot (*Fusarium oxysporum*) of a sweet potato, black mold (*Aspergillus niger*) of an onion, soft rot (*Rhizopus nigricans*) of a sweet potate, 'bakanae' disease (*Gibberella fujikuroi*) of a paddy rice, powdery mildew (*Erysiphe graminis*) of a barley and a wheat, powdery mildew (*Sphaerotheca flugina*) of a cucumber, powdery mildew (*Podosphaera leucotroicha*) of an apple, powdery mildew (*Uncinula necator*) of a grape, powdery mildew of other host plants, leaf rust (*Puccina recondita*) of a wheat, crown rust (*Puccina coronate*) of oats and rust of other host plants. The hydroxylamine derivatives are especially useful as seed disinfectants.

As the industrial fungicides, the hydroxyamino derivatives exhibit the fungicidal activity especially against woodrot fungi such as *Tyromyces palustris*, *Coriolus versicolor* and *Selupula lacrymas*, and are useful as wood preservatives of plywoods, wood products and woody products such as particle boards and fiber boards, as preservatives and fungicides of pulp production water, plastic products and paints, as preservatives of toiletries and leather products, and as clothing fungicides.

As the medical fungicides, the hydroxyamino derivatives are useful for the disinfection of hands and legs of humans and animals as well as for the treatment of local fungal infection, mucous membrane infection and systematic fungal infection which are caused by microorganisms of the genera Trichophyton, Candida, Aspergills and the like.

The agricultural and industrial fungicides containing the hydroxylamine derivatives of the formula (I) in the present invention as an active ingredient may be used in the appropriate formulation. For example, it is advisable that the active ingredient be mixed in an appropriate amount with a suitable inert carrier and, as required, with an adjuvant to conduct dissolution, dispersion, suspension, mixing, dipping, adsorption or absorption and the mixture be formulated into a solution, a suspension, an oil, an emulsion, a dust, a granule, a wettable powder, a wettable granule, a pellet, a paste, an aerosol or the like.

The inert carrier which can be used in the present invention may be solid, liquid or gaseous. Examples of the solid carrier include a soybean flour, a wood flour, a bark flour, a sawdust, a tobacco stalk flour, a walnut shell flour, a wheat bran flour, a cellulose powder, a residue obtained after formation of a food extract, synthetic polymers such as pulverized synthetic resins, clays (for example, kaolin, bentonite and acid clay), talcs (for example, talc and pyrophyllite), silicas (for example, diatonaceous earth, quartz sand, mica, synthetic silicate salt and high-dispersion synthetic silicic acid), activated carbon, sulfur powder, pumice stone, calcined diatomaceous earth, brick pulverization product, fly ash, sand, inorganic mineral powder of calcium carbonate or calcium phosphate, chemical fertilizer or compost of ammonium sulfate, ammonium phosphate, ammonium nitrate, ammonium chloride or urea. These are used either singly or in combination.

The liquid carrier includes one having itself a solvent effect and one free from a solvent effect but can disperse the active ingredient using an adjuvant. Examples of the liquid carrier include water; alcohols such as methyl alcohol, isopropanol and ethylene glycol; ketones such as acetone and cyclohexanone; ethers such as ethyl ether, dioxane, tetrahydrofuran and cellosolve; aliphatic hydrocarbons such as gasoline and kerosene; aromatic hydrocarbons such as benzene, toluene, solvent naphtha and methylnaphthalene; halogenated hydrocarbons such as dichloroethane and chloroform; esters such as ethyl acetate and diisopropyl phthalate; amides such as dimethylformamide and dimethylacetamide; nitriles such as acetonitrile; and dimethyl sulfoxide. These compounds are used either singly or in combination.

Examples of the gaseous carrier include freon, butane gas, dimethyl ether, carbon dioxide gas and LPG (liquefied petroleum gas).

The adjuvant is used according to the purpose. A surfactant can be used to emulsify, disperse, solubilize or wet the active ingredient compound. Examples of the surfactant include polyoxyethylene alkylaryl ethers, polyoxyethylene alkyl ethers, polyoxyethylene higher fatty acid esters, polyoxyethylene resin acid esters, polyoxyethylene solvitan monooleate, alkylallylsorbitan monolaurates, alkylbenzenesulfonates, alkylnaphthalene sulfonates, lignin sulfonate and higher alcohol sulfonate esters. These are used either singly or in combination. No adjuvant is used in some cases.

The adjuvant can be used to stabilize dispersion of the active ingredient compound and to adhere or bind the active ingredient compound. Examples of such an adjuvant include casein, gelatin, starch, alginic acid, CMC, gum arabic, agar, polyvinyl alcohol, wood turpentine oil, rice bran oil, bentonite, lignin and sulfite liquor.

The adjuvant can be used to improve fluidity of the solid product. Examples of such an adjuvant include waxes, stearic acid and alkyl phosphates.

The adjuvant can be used as a peptizer (deflocculant) of a dispersible product. Examples of such an adjuvant include a naphthalenesulfonic acid condensate and a phosphate salt.

A defoamer such as a silicone oil can also be added.

When the dihydroxylamine derivatives of the formula (I) in the present invention are used as agricultural and horticultural fungicides, the amount of the active ingredient varies depending on various factors such as purposes, crops, growth conditions of crops, route of disease emergence, weather, environmental conditions, formulation, application method, application position, application period and the like. However, it is appropriately selected from the range of from 0.1 g to 1 kg per 10 ares.

The amount of the active ingredient can be adjusted as required. In the case of a dust or a powder, it is usually between 0.5 and 20%. In the case of an emulsifiable concentrate, a suspension or a wettable powder, it is between 0.1 and 90%.

The agricultural and horticultural fungicides of the present invention can also be used by being mixed with other agricultural and horticultural fungicides in order to broaden the range of diseases to be controlled and the control period and to decrease the dose of the chemical agent. The agricultural and horticultural fungicides containing the compounds of the present invention as the active ingredient exhibit marked fungicidal activity against the above-mentioned diseases that damage paddy land crops, upland crops, fruit trees, vegetables, other crops, flowers and the like. Accordingly, these fungicides are applied to water, a foliage (stems and leaves) and a soil of a paddy land, an upland, fruit trees, vegetables, other crops, flowers and the like before or at the time of emergence of diseases, making it possible to bring forth desired effects of the fungicides of the present invention.

When the hydroxylamine derivatives of the formula (I) in the present invention are used as wood preservatives, a lumber is surface-treated by coating, spraying, dipping or the like or is treated by pressure injection, vacuum injection or the like, as it is or by being diluted with water or the like. Moreover, by adding the hydroxylamine derivatives to a plywood adhesive, the hydroxylamine derivatives of the present invention can be applied to building materials in particular, as an agent for preventing wood-rot fungi.

The amount of the chemical agent ordinarily varies with the type of preparations, the application period, the application position, the application method, the type of the wood-rot fungi, the extent of the damage and the like. The chemical agent containing the active ingredient is ordinarily used in an amount of from 0.1 to 40 g per square meter of a lumber.

When the hydroxylamine derivatives of the present invention are used as wood preservatives, these may be used by being mixed with other wood preservatives, an insecticide, an acaricide, an ant-killing agent, a disinfectant and a synergist. Examples of the common wood preservatives include 3-iodo-2-propynylbutyl carbamate, 3-iodopropargyl and zinc naphthenate. Examples of the Ant killing agent include Chlorpyrifos, Phoxim, fenitrothion, Permethrin, cypermethrin and fenvalerate.

When the hydroxylamine derivatives of formula (I) in the present invention are used as medical fungicide, these may be used either singly or in the form of a composition containing a pharmaceutically acceptable inert carrier or diluent, and take the form which is suitable for oral or parenteral administration, such as a liquid, a tablet, a suppository, an emulsifier, an ointment, a cream, a lotion or a cataplasm (poultice). The preparation may contain an aid, a stabilizer, a wetting agent, an emulsifying agent, a buffer, and other ordinary additives. The compound can be administered at a dose of from 0.05 to 100 mg, preferably from 0.5 to 50 mg per kilogram of a weight of an adult for a day in the systematic treatment. The optimum concentration of the active ingredient in the local treatment is between 0.001 and 5%, preferably between 0.1 and 2%.

EXAMPLES

The present invention will be illustrated specifically by referring to Examples, Formulation Examples and Test Examples. However, the present invention is not limited thereto.

Example 1
Production of methyl N-methoxy-N-iodopropargylcarbamate (Compound No. 1)

0.43 g of sodium hydride (60% in oil) was suspended in 10 ml of tetrahydrofuran, and 1.0 g of methyl N-methoxycarbamate and 1.36 g of propargyl bromide were added to the suspension in this order while being cooled with ice. The mixture was heat-refluxed for 4 hours. After completion of the reaction, water was added to the reaction solution, and the mixture was extracted with ethyl acetate. The extract was dried, concentrated and purified by silica gel column chromatography to obtain 0.8 g of methyl N-methoxy-N-propargylcarbamate.

0.5 g of methyl N-methoxy-N-propargylcarbamate thus obtained was dissolved in 5 ml of N,N-dimethylformamide. 1.8 g of iodine and 5 ml of N,N-dimethylformamide containing a catalytic amount of a saturated aqueous solution of potassium iodide were added thereto. 2.0 g of a 30% potassium hydroxide aqueous solution were added thereto dropwise while being cooled with ice. The mixture was stirred at room temperature for 2 hours. After completion of the reaction, water was added to the reaction solution, and the mixture was extracted with ethyl acetate. The extract was washed with a saturated aqueous solution of sodium thiosulfate and then with water, dried and concentrated to obtain 0.6 g of methyl N-methoxy-N-iodopropargylcarbamate.

$^1$H-NMR ($\delta$ in $CDCl_3$) 3.78 (s; 3H), 3.81 (s; 3H), 4.39 (s; 2H)

Example 2
Production of methyl N-methoxy-N-iodopropargyloxymethylcarbamate (Compound No. 94)

0.37 g of sodium hydride (60% in oil) was suspended in 10 ml of tetrahydrofuran, and 0.8 g of methyl N-methoxycarbamate and 0.96 g of chloromethylpropargyl ether were added thereto in this order while being cooled with ice. The mixture was heat-refluxed for 1 hour. After completion of the reaction, water was added to the reaction solution, and the mixture was extracted with ethyl acetate. The extract was dried, concentrated and purified by silica gel column chromatography to obtain 1.0 g of methyl N-methoxy-N-propargyloxymethylcarbamate.

0.5 g of methyl N-methoxy-N-propargyloxymethylcarbamate thus obtained was dissolved in 5 ml of N,N-dimethylformamide. 1.5 g of iodine and 5 ml of N,N-dimethylformamide containing a catalytic amount of a saturated aqueous solution of potassium iodide were added to the solution, and 1.6 g of a 30% potassium hydroxide aqueous solution were added thereto while being cooled with ice. The mixture was stirred at room temperature for 2 hours. After completion of the reaction, water was added to the reaction solution, and the mixture was extracted with ethyl acetate. The extract was washed with a saturated aqueous solution of sodium thiosulfate and then with water, dried, and concentrated to obtain 0.7 g of methyl N-methoxy-N-iodopropargyloxymethylcarbamate.

$^1$H-NMR (δ in CDCl$_3$) 3.78 (s; 3H), 3.82 (s; 3H), 4.42 (s; 2H), 5.04 (s; 2H)

Example 3
Production of N-methoxy-N-iodopropargyl-p-chlorobenzamide (Compound No. 57)

0.22 g of sodium hydride (60% in oil) was suspended in 10 ml of tetrahydrofuran, and 1.0 g of N-methoxy-p-chlorobenzamide and 0.68 g of propargyl bromide were added thereto in this order while being cooled with ice. The mixture was heat-refluxed for 8 hours. After completion of the reaction, water was added to the reaction solution, and the mixture was extracted with ethyl acetate. The extract was dried, concentrated and purified by silica gel column chromatography to obtain 0.44 g of N-methoxy-N-propargyl-p-chlorobenzamide.

0.44 g of N-methoxy-N-propargyl-p-chlorobenzamide thus obtained was dissolved in 5 ml of N,N-dimethylformamide. 1.5 g of iodine and 5 ml of N,N-dimethylformamide containing a catalytic amount of a saturated aqueous solution of potassium iodide were added to the solution, and 1.8 g of a 30% potassium hydroxide aqueous solution were added thereto while being cooled with ice. The mixture was stirred at room temperature for 2 hours. After completion of the reaction, water was added to the reaction solution, and the mixture was extracted with ethyl acetate. The extract was washed with a saturated aqueous solution of sodium thiosulfate and then with water, dried, and concentrated to obtain 0.47 g of N-methoxy-N-iodopropargyl-p-chlorobenzamide.

$^1$H-NMR (δ in CDCl$_3$) 3.67 (s; 3H), 4.66 (s; 2H), 7.40 (d; 2H), 7.69 (d: 2H)

Example 4
Production of iodopropargyl N-methoxy-2,4-dichlorobenzimidate (Compound No. 130)

1.0 g of N-methoxy-2,4-dichlorobenzamide, 0.75 g of potassium carbonate and 0.65 g of propargyl bromide were added to 10 ml of N,N-dimethylformamide, and the mixture was stirred for 3 hours. After completion of the reaction, water was added to the reaction solution, and the mixture was extracted with ethyl acetate. The extract was dried, concentrated and purified by silica gel column chromatography to obtain 0.35 g of propargyl N-methoxy-2,4-dichlorobenzimidate.

0.35 g of propargyl N-methoxy-2,4-dichlorobenzimidate thus obtained was dissolved in 5 ml of N,N-dimethylformamide, and 1.0 g of iodine and 5 ml of N,N-dimethylformamide containing a catalytic amount of a potassium iodide aqueous solution were added thereto. 1.3 g of 30% potassium hydroxide aqueous solution was added thereto dropwise while being cooled with ice, and the mixture was stirred at room temperature for 1 hour. After completion of the reaction, water was added to the reaction solution, and the mixture was extracted with ethyl acetate. The extract was washed with a saturated aqueous solution of sodium thiosulfate and then with water, dried and concentrated to obtain 0.47 g of iodopropargyl N-methoxy-2,4-dichlorobenzimidate.

$^1$H-NMR (δ in CDCl$_3$) 3.93 (s; 3H), 4.73 (s; 2H), 7.3–7.5 (m; 3H)

Example 5
Production of iodopropargyl N-methoxy-p-chlorobenzimidate (Compound No. 125)

1.0 g of N-methoxy-p-chlorobenzamide was dissolved in 10 ml of carbon tetrachloride, and 1.2 g of phosphorus tetrachloride were added thereto. The mixture was heat-refluxed for 3 hours. The reaction solution was washed with water, dried, and concentrated to obtain 0.61 g of 4,α-dichlorobenzaldehyde oxime O-methyl ether.

0.18 g of propargyl alcohol was dissolved in 5 ml of tetrahydrofuran, and 0.13 g of sodium hydride (60% in oil) were added thereto while being cooled with ice. A solution of 0.61 g of 4,α-dichlorobenzaldehyde oxime O-methyl ether in 5 ml of tetrahydrofuran was added thereto dropwise. The mixture was heat-refluxed for 6 hours, and water was then added to the reaction solution. The mixture was extracted with ethyl acetate. The extract was dried, concentrated and purified by silica gel column chromatography to obtain 0.59 g of propargyl N-methoxy-p-chlorobenzimidate.

0.59 g of propargyl N-methoxy-p-chlorobenzimidate thus obtained was dissolved in 5 ml of N,N-dimethylformamide, and 2.0 g of iodine and 5 ml of N,N-dimethylformamide containing a catalytic amount of a saturated aqueous solution of potassium iodide were added thereto. 2.5 g of a 30% potassium hydroxide aqueous solution was added thereto dropwise while being cooled with ice. The mixture was stirred at room temperature for 3 hours. After completion of the reaction, water was added to the reaction solution, and the mixture was extracted with ethyl acetate. The extract was washed with a saturated aqueous solution of sodium thiosulfate and then with water, dried, and concentrated to obtain 0.78 g of iodopropargyl N-methoxy-p-chlorobenzimidate.

$^1$H-NMR (δ in CDCl$_3$) 3.92 (s; 3H), 5.10 (s; 2H), 7.34 (d; 2H), 7.69 (d; 2H)

Example 6
Production of N-methoxy-N-iodopropargyloxymethylbenzamide (Compound No. 103)

0.6 g of N-methoxybenzamide was dissolved in 10 ml of acetonitrile, and 0.55 g of potassium carbonate and 0.42 g of chloromethylpropargyl ether were added thereto in this order. The mixture was stirred at room temperature for 3 hours. After completion of the reaction, water was added to the reaction solution, and the mixture was extracted with ethyl acetate. The extract was dried, concentrated and purified by silica gel column chromatography to obtain 0.8 g of N-methoxy-N-propargyloxymethylbenzamide.

0.8 g of N-methoxy-N-propargyloxymethylbenzamide thus obtained was dissolved in 5 ml of methanol, and 0.85 g of a 30% sodium hydroxide aqueous solution were added thereto. A solution of 0.41 g of iodine monochloride in 5 ml of methanol was added thereto dropwise while being cooled with ice, and the mixture was stirred at room temperature for 1 hour. After completion of the reaction, water was added to the reaction solution, and the mixture was extracted with ethyl acetate. The extract was washed with a saturated aqueous solution of sodium thiosulfate and then with water, dried, and concentrated to obtain 0.7 g of N-methoxy-N-iodopropargyloxymethylbenzamide.

$^1$H-NMR (δ in CDCl$_3$) 3.93 (s; 3H), 4.58 (s; 2H), 5.40 (s; 2H), 7.3–7.5 (m; 3H) 7.6–7.8 (m; 2H)

Example 7
Production of N-methoxy-N-iodopropargyloxymethylbenzenesulfonamide (Compound No. 118)

0.6 g of N-methoxybenzenesulfonamide was dissolved in 10 ml of acetonitrile, and 0.44 g of potassium carbonate and 0.34 g of chloromethylpropargyl ether were added thereto in this order. The mixture was stirred at room temperature for 4 hours. After completion of the reaction, water was added to the reaction solution, and the mixture was extracted with ethyl acetate. The extract was dried, concentrated, and purified by silica gel column chromatography to obtain 0.7 g of N-methoxy-N-propargyloxymethylbenzenesulfonamide.

0.5 g of N-methoxy-N-propargyloxymethylbenzenesulfonamide thus obtained was dissolved in 5 ml of N,N-dimethylformamide, and 1.5 g of iodine and 5 ml of N,N-dimethylformamide containing a catalytic amount of a saturated aqueous solution of potassium iodide were added thereto. 1.8 g of a 30% potassium hydroxide aqueous solution was added thereto dropwise while being cooled with ice. The mixture was stirred at room temperature for 3 hours. After completion of the reaction, water was added to the reaction solution, and the mixture was extracted with ethyl acetate. The extract was washed with a saturated aqueous solution of sodium thiosulfate and then with water, dried and concentrated to obtain 0.6 g of N-methoxy-N-iodopropargyloxymethylbenzenesulfonamide.

$^1$HMR-NMR (δ in CDCl$_3$) 3.89 (s; 3H), 4.31 (s; 2H), 4.70 (s; 2H), 7.5–8.0 (m; 5H)

The typical examples of the compounds in the present invention which were prepared in the same manner as in Examples 1 to 7 are shown in Table 1. However, the present invention is not limited thereto. In Table 1, Ph represents a phenyl group, c-C$_3$H$_5$ represents a cyclopropyl group, and c-C$_6$H$_{11}$, represents a cyclohexyl group. The parenthesized figure of the refractive index indicates a temperature (°C.).

TABLE 1a

In the formula (I), $$R^1O\diagdown N\text{-(C-O)}_n\text{-C-C}\equiv CI$$
$$R^2X\diagup$$

$R = -N-OR^1$, $R^3 = R^4 = R^5 = R^6 = H$, with $XR^2$

| No. | R$^1$ | R$^2$ | X | n | Physical property (*) |
|---|---|---|---|---|---|
| 1 | CH$_3$ | CH$_3$ | CO$_2$ | 0 | nD 1.535(20° C.) |
| 2 | i-C$_3$H$_7$ | CH$_3$ | CO$_2$ | 0 | nD 1.507(17° C.) |
| 3 | 3-Cl(CH$_2$)$_3$ | CH$_3$ | CO$_2$ | 0 | |
| 4 | H$_2$C=CHCH$_2$ | CH$_3$ | CO$_2$ | 0 | nD 1.526(17° C.) |
| 5 | HC≡CCH$_2$ | CH$_3$ | CO$_2$ | 0 | |
| 6 | IC≡CCH$_2$ | CH$_2$ | CO$_2$ | 0 | |
| 7 | n-C$_4$H$_9$ | CH$_3$ | CO$_2$ | 0 | nD 1.514(16° C.) |
| 8 | i-C$_4$H$_9$ | CH$_3$ | CO$_2$ | 0 | |
| 9 | c-C$_6$H$_{11}$ | CH$_3$ | CO$_2$ | 0 | |
| 10 | C$_2$H$_5$OCH$_2$CH$_2$ | CH$_3$ | CO$_2$ | 0 | nD 1.517(16° C.) |
| 11 | C$_2$H$_5$SCH$_2$CH$_2$ | CH$_3$ | CO$_2$ | 0 | |
| 12 | C$_2$H$_5$SO$_2$CH$_2$CH$_2$ | CH$_3$ | CO$_2$ | 0 | |
| 13 | n-C$_{12}$H$_{25}$ | CH$_3$ | CO$_2$ | 0 | nD 1.486(13° C.) |
| 14 | Ph | CH$_3$ | CO$_2$ | 0 | |
| 15 | PhCH$_2$ | CH$_3$ | CO$_2$ | 0 | nD 1.571(16° C.) |
| 16 | CH$_3$ | FCH$_2$CH$_2$ | CO$_2$ | 0 | |
| 17 | CH$_3$ | ClCH$_2$CH$_2$ | CO$_2$ | 0 | |
| 18 | CH$_3$ | c-C$_3$H$_5$ | CO$_2$ | 0 | |
| 19 | CH$_3$ | n-C$_4$H$_9$ | CO$_2$ | 0 | nD 1.508(26° C.) |
| 20 | CH$_3$ | i-C$_4$H$_9$ | CO$_2$ | 0 | nD 1.498(18° C.) |
| 21 | CH$_3$ | c-C$_6$H$_{11}$ | CO$_2$ | 0 | |
| 22 | CH$_3$ | n-C$_{12}$H$_{25}$ | CO$_2$ | 0 | |
| 23 | CH$_3$ | 2-C$_2$H$_5$-n-C$_6$H$_{11}$ | CO$_2$ | 0 | nD 1.483(26° C.) |
| 24 | CH$_3$ | CCl$_3$CH$_2$ | CO$_2$ | 0 | nD 1.546(18° C.) |
| 25 | CH$_3$ | CF$_3$CH$_2$ | CO$_2$ | 0 | |
| 26 | CH$_3$ | CH$_3$OCH$_2$CH$_2$ | CO$_2$ | 0 | nD 1.478(20° C.) |
| 27 | CH$_3$ | PhOCH$_2$CH$_2$ | CO$_2$ | 0 | |
| 28 | CH$_3$ | CH$_3$SCH$_2$CH$_2$ | CO$_2$ | 0 | |
| 29 | CH$_3$ | CH$_3$SO$_2$CH$_2$CH$_2$ | CO$_2$ | 0 | |
| 30 | CH$_3$ | Ph | CO$_2$ | 0 | |
| 31 | CH$_3$ | PhCH$_2$ | CO$_2$ | 0 | |
| 32 | n-C$_4$H$_9$ | i-C$_4$H$_9$ | CO$_2$ | 0 | nD 1.487(20° C.) |
| 33 | C$_2$H$_5$OCH$_2$CH$_2$ | i-C$_4$H$_9$ | CO$_2$ | 0 | nD 1.493(17° C.) |
| 34 | PhCH$_2$ | i-C$_4$H$_9$ | CO$_2$ | 0 | nD 1.538(20° C.) |
| 35 | 4-Cl—PhCH$_2$ | CH$_3$ | CO$_2$ | 0 | nD 1.568(25° C.) |
| 36 | 4-CH$_3$—PhCH$_2$ | CH$_3$ | CO$_2$ | 0 | nD 1.562(25° C.) |
| 37 | PhCH$_2$CH$_2$ | CH$_3$ | CO$_2$ | 0 | nD 1.548(25° C.) |

TABLE 1a-continued $$R^{10}\diagdown N\text{-}(C\text{-}O)_n\text{-}C\text{-}C\equiv Cl$$
with $R^2X$ and H's In the formula (I), $R = -N-OR^1$, $R^3 = R^4 = R^5 = R^6 = H$, $XR^2$

| No. | R¹ | R² | X | n | Physical property (*) |
|---|---|---|---|---|---|
| 38 | PhCH=CHCH₂ | CH₃ | CO₂ | 0 | nD 1.586(25° C.) |
| 39 | CH₃ | n-C₃H₇ | CO | 0 | nD 1.524(13° C.) |
| 40 | CH₃ | c-C₃H₅ | CO | 0 | nD 1.546(26° C.) |
| 41 | CH₃ | 3-Cl(CH₂)₃ | CO | 0 |  |
| 42 | CH₃ | i-C₄H₉ | CO | 0 | nD 1.507(24° C.) |
| 43 | CH₃ | n-C₅H₁₁ | CO | 0 | nD 1.512(26° C.) |
| 44 | CH₃ | 1-C₂H₅-n-C₅H₁₀ | CO | 0 | nD 1.513(24° C.) |
| 45 | CH₃ | n-C₇H₁₅ | CO | 0 | nD 1.501(26° C.) |
| 46 | CH₃ | C≡CH | CO | 0 |  |
| 47 | CH₃ | C≡Cl | CO | 0 |  |
| 48 | CH₃ | CH₂OC₂H₅ | CO | 0 |  |
| 49 | CH₃ | CH₂SC₃H₇-n | CO | 0 |  |
| 50 | CH₃ | CH₂SO₂C₃H₇-n | CO | 0 |  |
| 51 | CH₃ | CH₂N(CH₃)₂ | CO | 0 |  |
| 52 | CH₃ | Ph | CO | 0 | m.p. 83–86° C. |
| 53 | CH₃ | 4-NO₂—Ph | CO | 0 | paste |
| 54 | CH₃ | 2-CO₂CH₃—Ph | CO | 0 | nD 1.576(21° C.) |
| 55 | CH₃ | 2-CF₃—Ph | CO | 0 | nD 1.526(24° C.) |
| 56 | CH₃ | 2-Cl—Ph | CO | 0 | m.p. 93–94° C. |
| 57 | CH₃ | 4-Cl—Ph | CO | 0 | m.p. 100–101° C. |
| 58 | CH₃ | 4-Br—Ph | CO | 0 | nD 1.615(19° C.) |
| 59 | CH₃ | 4-F—Ph | CO | 0 | nD 1.571(19° C.) |
| 60 | CH₃ | 4-CH₃—Ph | CO | 0 | nD 1.574(21° C.) |
| 61 | CH₃ | 4-t-C₄H₉—Ph | CO | 0 | nD 1.563(15° C.) |
| 62 | CH₃ | 4-CH₃O—Ph | CO | 0 | paste |
| 63 | CH₃ | 2,6-F₂—Ph | Co | 0 | nD 1.532(25° C.) |
| 64 | CH₃ | 4-CH₃S—Ph | CO | 0 |  |
| 65 | CH₃ | 4-CH₃SO₂—Ph | CO | 0 |  |
| 66 | CH₃ | 4-CF₃—Ph | CO | 0 |  |
| 67 | CH₃ | 4-CF₃O—Ph | CO |  |  |
| 68 | CH₃ | 4-CN—Ph | CO | 0 |  |
| 69 | CH₃ | 4-PhO—Ph | CO | 0 |  |
| 70 | CH₃ | 4-(CH₃)₂N—Ph | CO | 0 |  |
| 71 | CH₃ | 2,4-Cl₂—Ph | CO | 0 | m.p. 156–157° C. |
| 72 | CH₃ | 3,5-Cl₂—Ph | CO | 0 | nD 1.589(21° C.) |
| 73 | CH₃ | 2-naphthyl | CO | 0 |  |
| 74 | CH₃ | 2-pyridyl | CO | 0 |  |
| 75 | CH₃ | 3-pyridyl | CO | 0 | m.p. 110–115° C. |
| 76 | CH₃ | 4-pyridyl | CO | 0 |  |
| 77 | CH₃ | 2-furyl | CO | 0 | m.p. 92–93° C. |
| 78 | CH₃ | 2-thienyl | CO | 0 | m.p. 83–85° C. |
| 79 | CH₃ | PhCH₂ | CO | 0 | nD 1.578(24° C.) |
| 80 | CH₃ | 4-Cl—PhCH₂ | CO | 0 |  |
| 81 | CH₃ | 4-CH₃—PhCH₂ | CO | 0 |  |
| 82 | CH₃ | PhOCH₂ | CO | 0 | nD 1.591(24° C.) |
| 83 | CH₃ | 4-Cl—PhOCH₂ | CO | 0 |  |
| 84 | CH₃ | 2,4-Cl₂—PhOCH₂ | CO | 0 |  |
| 85 | n-C₄H₉ | n-C₃H₇ | Co | 0 | nD 1.518(25° C.) |
| 86 | i-C₄H₉ | n-C₃H₇ | CO | 0 |  |
| 87 | c-C₆H₁₁ | n-C₃H₇ | CO | 0 |  |
| 88 | (CH₃)₂NCH₂ | n-C₃H₇ | CO | 0 |  |
| 89 | Ph | CH₃ | CO | 0 |  |
| 90 | PhCH₂ | n-C₃H₇ | CO | 0 | nD 1.564(13° C.) |
| 91 | PhCH₂ | t-C₄H₉ | CO | 0 | nD 1.547(14° C.) |
| 92 | PhCH₂ | CH₂OC₂H₅ | CO | 0 |  |
| 93 | PhCH₂ | Ph | CO | 0 | nD 1.608(15° C.) |
| 94 | CH₃ | CH₃ | CO₂ | 1 | nD 1.510(16° C.) |
| 95 | CH₃ | i-C₄H₉ | CO₂ | 1 | nD 1.492(22° C.) |
| 96 | CH₃ | CCl₃CH₂ | CO₂ | 1 | nD 1.534(22° C.) |
| 97 | n-C₄H₉ | i-C₄H₉ | CO₂ | 1 | nD 1.498(22° C.) |
| 98 | C₂H₅OCH₂CH₂ | CH₃ | CO₂ | 1 | nD 1.505(22° C.) |
| 99 | PhCH₂ | CH₃ | CO₂ | 1 | nD 1.537(22° C.) |
| 100 | PhCH₂ | i-C₄H₉ | CO₂ | 1 | nD 1.533(22° C.) |
| 101 | CH₃ | c-C₃H₅ | CO | 1 |  |
| 102 | CH₃ | 3-Cl(CH₂)₃ | CO | 1 | nD 1.527(21° C.) |
| 103 | CH₃ | Ph | CO | 1 | nD 1.509(28° C.) |
| 104 | CH₃ | 2-Cl—Ph | CO | 1 | nD 1.574(21° C.) |
| 105 | CH₃ | 4-Cl—Ph | CO | 1 | nD 1.581(21° C.) |
| 106 | CH₃ | 4-F—Ph | CO | 1 |  |

TABLE 1a-continued

In the formula (I), $R = -N-OR^1$, $R^3 = R^4 = R^5 = R^6 = H$ $$\begin{array}{c} R^1O \\ \phantom{xx} \diagdown \\ \phantom{xxxx} N+C-O)_n-C-C\equiv CI \\ \phantom{xx} \diagup \\ R^2X \end{array}$$

| No. | $R^1$ | $R^2$ | X | n | Physical property (*) |
|---|---|---|---|---|---|
| 107 | $CH_3$ | $4-CH_3-Ph$ | CO | 1 | nD 1.571(21° C.) |
| 108 | $CH_3$ | $4-NO_2-Ph$ | Co | 1 | m.p. 98–100° C. |
| 109 | $CH_3$ | $3,5-Cl_2-Ph$ | CO | 1 | m.p. 52–53° C. |
| 110 | $CH_3$ | $2,6-F_2-Ph$ | CO | 1 | paste |
| 111 | $CH_3$ | $PhCH=CHCH_2$ | CO | 1 | |
| 112 | $CH_3$ | $n-C_5H_{11}$ | CO | 1 | nD 1.560(28° C.) |
| 113 | $CH_3$ | $n-C_7H_{15}$ | CO | 1 | nD 1.507(15° C.) |

(* melting point or refractive index)

TABLE 1b

In the formula (I), $R = -N-OR^1$ $$\begin{array}{c} R^1O \phantom{xxx} R^3 \phantom{xxx} R^5 \\ \phantom{xx} \diagdown \phantom{xx} | \phantom{xxx} | \\ \phantom{xxxx} N+C-O)_n-C-C\equiv CI \\ \phantom{xx} \diagup \phantom{xx} | \phantom{xxx} | \\ R^2X \phantom{xxxx} R^4 \phantom{xxx} R^6 \end{array}$$

| No. | $R^1$ | $R^2$ | $R^3$ | $R^4$ | $R^5$ | $R^6$ | X | n | Physical property (*) |
|---|---|---|---|---|---|---|---|---|---|
| 114 | $CH_3$ | $i-C_4H_9$ | H | H | $CH_3$ | $CH_3$ | $CO_2$ | 1 | nD 1.489(16° C.) |
| 115 | $CH_3$ | $4-Cl-Ph$ | H | H | $CH_3$ | $CH_3$ | CO | 1 | nD 1.548(21° C.) |
| 116 | $CH_3$ | $4-Cl-Ph$ | $CH_3$ | H | H | H | CO | 1 | |
| 117 | $CH_3$ | Ph | H | H | H | H | $SO_2$ | 0 | paste |
| 118 | $CH_3$ | Ph | H | H | H | H | $SO_2$ | 1 | nD 1.550(28° C.) |
| 119 | $CH_3$ | $4-CH_3-Ph$ | H | H | H | H | $SO_2$ | 0 | m.p. 57–58° C. |

(* melting point or refractive index)

TABLE 1c

In the formula (Ic), $R^3 = R^4 = R^5 = R^6 = H$, n = 0

$$R^1O-N=C-O-\underset{\underset{H}{|}}{\overset{\overset{R^2}{|}}{C}}-C\equiv CI$$

| No. | $R^1$ | $R^2$ | Physical property (melting point or refractive index) |
|---|---|---|---|
| 120 | $CH_3$ | Ph | nD 1.585(28° C.) |
| 121 | $n-C_3H_7$ | Ph | |
| 122 | $i-C_4H_9$ | Ph | |
| 123 | $PhCH_2CH_2$ | Ph | |
| 124 | $CH_3$ | $2-Cl-Ph$ | nD 1.593(19° C.) |
| 125 | $CH_3$ | $4-Cl-Ph$ | nD 1.584(17° C.) |
| 126 | $CH_3$ | $4-Br-Ph$ | m.p. 56–57° C. |
| 127 | $CH_3$ | $4-F-Ph$ | nD 1.576(19° C.) |
| 128 | $CH_3$ | $4-CH_3-Ph$ | nD 1.582(21° C.) |
| 129 | $CH_3$ | $4-NO_2-Ph$ | m.p. 88–90° C. |
| 130 | $CH_3$ | $2,4-Cl_2-Ph$ | nD 1.596(24° C.) |
| 131 | $CH_3$ | $3,5-Cl_2-Ph$ | m.p. 50–51° C. |
| 132 | $CH_3$ | $2,6-F_2-Ph$ | nD 1.549(25° C.) |

The $^1$HNMR ($\delta$ in $CDCl_3$) data of the pastes among the compounds shown in the Tables are mentioned below.

Compound of No. 53: 3.66 (s; 3H), 4.70 (s; 2H), 7.88 (d; 2H), 8.29 (d; 2H)

Compound of No. 62: 3.70 (s; 3H), 3.86 (s; 3H), 4.65 (s; 2H), 6.92 (d; 2H), 7.76 (d; 2H)

Compound of No. 110: 3.94 (s; 3H), 4.50 (s; 2H), 5.11 (s; 2H), 6.9–7.0 (m; 2H), 7.3–7.5 (m; 1H)

Compound of No. 117: 3.91 (s; 3H), 4.02 (s; 2H), 7.5–7.7 (m; 3H), 7.9–8.0 (m; 2H)

In the following Formulation Examples, parts are parts by weight.

| Formulation Example 1 | parts |
|---|---|
| Compound of the present invention | 50 |
| Xylene | 40 |
| Mixture of polyoxyethylenenonylphenyl ether and alkylbenzenesulfonic acid | 10 |

The above ingredients were uniformly mixed and dissolved to form an emulsion.

| Formulation Example 2 | parts |
|---|---|
| Compound of the present invention | 0.5 |
| Xylene | 0.8 |
| Illuminating kerosine | 98.7 |

The above ingredients were uniformly mixed and dissolved to form a lubricant.

| Formulation Example 3 | parts |
|---|---|
| Compound of the present invention | 3 |
| Clay powder | 82 |
| Diatomaceous earth powder | 15 |

The above ingredients were uniformly mixed and pulverized to form a dust.

| Formulation Example 4 | parts |
|---|---|
| Compound of the present invention | 5 |
| Mixed powder of bentonite and clay | 90 |
| Calcium stearate | 1 |

The above ingredients were uniformly mixed, kneaded with an appropriate amount of water, granulated and dried to form granules.

| Formulation Example 5 | parts |
|---|---|
| Compound of the present invention | 20 |
| Mixture of kaolin and high-dispersion synthetic silicic acid | 75 |
| Mixture of polyoxyethylenenonylphenyl ether and calcium alkylbenzenesulfonate | 5 |

The above ingredients were uniformly mixed and pulverized to form a wettable powder.

| Formulation Example 6 | parts |
|---|---|
| Compound of the present invention | 1 |
| Polyethylene glycol 400 | 99 |

The above-mentioned ingredients were mixed and dissolved to form a coating liquid.

| Formulation Example 7 | parts |
|---|---|
| Compound of the present invention | 2 |
| Polyethylene glycol 400 | 49 |
| Polyethylene glycol 4000 | 49 |

The above-mentioned ingredients were heat-mixed and dissolved, and then cooled to form an ointment.

| Formulation Example 8 | parts |
|---|---|
| Compound of the present invention | 3 |
| 1,2-propanediol | 5 |
| Glycerol stearate | 5 |
| Spermaceti | 5 |
| Isopropyl myristate | 10 |
| Polysorbate | 4 |

A mixture of the above ingredients was heated, and cooled. Then, 68 parts of water were added thereto while being stirred to form a cream.

Test Example 1

Test for effect to rice blast (Pyricularia oryzae) of a paddy field

A chemical solution (200 ppm) containing the compound of the present invention as an active ingredient was fully applied to a paddy rice (at 5-leaf stage) in a pot, and was air-dried. Subsequently, a suspension containing spores of rice plast (*Pyricularia oryzae*) of a paddy rice was sprayed thereto for inoculation.

After the inoculation, the pot was placed in a wet room of 20° C. for 1 day and in a green house for 6 days to cause full emergence of the disease. Then, the number of lesions in each leaf was measured, and a protective value in a treated lot was calculated in comparison to that in an untreated lot. The protective value was evaluated in terms of a protective effect according to the following evaluation standard. The results are shown in Table 2.

| Evaluation standard: | |
|---|---|
| Protective value (%) | Protective effect |
| 100–95 | A |
| 94–80 | B |
| 79–60 | C |
| 59–0 | — (blank) |

Test Example 2

Test for effect of disinfection of paddy rice seeds

A rough rice contaminated with *Gibberella fujikuroi* was dipped in a test agent which had been adjusted to a concentration of 1000 ppm at 25° C. for 24 hours. The thus-dipped rough rice was gently drained, sowed, and stimulated sprouting for 2 days. Three weeks later after the treatment with the chemical solution, the rate of the diseased seedling was measured, and the protective effect of the test agent was valuated in the same manner as in Test Example 1. The results are shown in Table 2.

TABLE 2

| | (Activity for preventing disearses) | |
|---|---|---|
| No. | Gibberella fujikuroi | Pyricularia oryzae |
| 2 | B | C |
| 4 | B | |
| 7 | C | |
| 10 | A | A |
| 13 | | B |
| 15 | | A |
| 19 | A | A |
| 20 | C | A |
| 23 | C | B |
| 24 | B | C |
| 26 | | B |
| 32 | | A |
| 33 | B | A |
| 34 | | A |
| 35 | C | A |
| 36 | C | A |
| 37 | A | A |
| 38 | B | A |
| 39 | C | |
| 40 | C | A |
| 42 | B | A |
| 43 | A | A |
| 45 | B | A |
| 52 | | A |
| 53 | B | |
| 54 | B | B |
| 55 | C | A |
| 57 | A | A |
| 60 | C | |
| 61 | | A |
| 62 | A | A |
| 63 | A | |
| 71 | | |
| 72 | B | A |
| 75 | | A |
| 79 | C | A |
| 82 | C | A |
| 85 | B | A |
| 90 | B | A |
| 91 | | A |
| 93 | | A |
| 94 | | |
| 95 | B | |
| 96 | B | A |

TABLE 2-continued (Activity for preventing diseases)

| No. | Gibberella fujikuroi | Pyricularia oryzae |
|---|---|---|
| 97 | B | A |
| 98 | A | |
| 99 | B | A |
| 100 | B | A |
| 102 | A | A |
| 103 | A | A |
| 104 | | A |
| 105 | B | A |
| 107 | C | A |
| 108 | B | A |
| 109 | B | A |
| 110 | A | A |
| 112 | A | |
| 113 | A | B |
| 114 | | C |
| 117 | A | A |
| 118 | A | A |
| 120 | A | |
| 125 | B | B |
| 128 | B | |
| 129 | C | A |
| 130 | B | A |
| 131 | | B |
| 132 | A | |

Test Example 3
Test for microbicidal activity against wood-rot fungi

The following test fungi were incubated in an agar culture medium. The resulting colonies were punched along with the agar by means of a cork borer having a diameter of 4 mm, and were used as an inoculation source. The test chemical agent was added to a barley extract agar culture medium at a concentration of 50 ppm, and the mixture was charged on a petri dish. The above-prepared inoculation source was put thereon, and incubated at a temperature of 28° C.±2° C. After from 2 to 10 days of the inoculation, the diameter of the colony of each fungus was measured, and a hypha growth inhibition ratio was calculated according to the following equation.

$$\text{Hypha growth inhibition ratio (\%)} = \frac{\text{diameter of hypha in an untreated lot} - \text{diameter of hypha in a test lot}}{\text{diameter of hypha in an untreated lot}} \times 100$$

The hypha growth inhibition ratio (%) was expressed in terms of microbicidal activity against the fungi as mentioned below. The results are shown in Table 3.

Evaluation standard:

| Hypha growth inhibition ratio (%) | Microbicidal activity |
|---|---|
| 100–95 | A |
| 94–80 | B |
| 79–60 | C |
| 59–0 | — (blank) |

Test fungi:
Basidiomycetes
 TYP: *Tyromyces palustris*
Deuteromycetes
 TRV: *Trichoderma viride*
Ascomycetes
 CHG: *Chaetomium globosum*

TABLE 3

(Bactericidal Activity)

| No. | TYP | TRV | CHG |
|---|---|---|---|
| 1 | A | A | A |
| 2 | A | A | A |
| 4 | A | A | A |
| 7 | A | A | A |
| 10 | A | A | A |
| 13 | | | |
| 15 | A | A | A |
| 19 | A | A | B |
| 20 | A | A | A |
| 23 | A | A | C |
| 24 | A | A | A |
| 26 | A | B | A |
| 32 | A | B | A |
| 33 | A | A | A |
| 34 | A | B | B |
| 35 | A | A | A |
| 36 | A | A | A |
| 37 | A | A | A |
| 38 | A | A | B |
| 39 | A | A | |
| 40 | A | A | B |
| 42 | A | A | A |
| 43 | A | A | B |
| 45 | A | A | B |
| 52 | A | A | |
| 53 | A | A | C |
| 54 | A | A | A |
| 55 | A | A | A |
| 57 | A | A | A |
| 60 | A | A | A |
| 61 | A | A | A |
| 62 | A | A | A |
| 63 | A | A | A |
| 71 | | B | |
| 72 | A | | |
| 75 | A | A | A |
| 79 | A | A | A |
| 82 | A | A | A |
| 85 | A | A | B |
| 90 | A | A | A |
| 91 | A | B | B |
| 93 | A | B | |
| 94 | A | A | A |
| 95 | A | A | A |
| 96 | A | A | A |
| 97 | A | A | B |
| 98 | A | A | A |
| 99 | A | A | A |
| 100 | A | A | |
| 102 | A | A | A |
| 103 | A | A | A |
| 104 | A | A | A |
| 105 | A | A | A |
| 107 | A | B | C |
| 108 | A | A | C |
| 109 | A | A | B |
| 110 | A | A | A |
| 112 | A | A | A |
| 113 | A | A | A |
| 114 | A | A | A |
| 117 | A | A | A |
| 118 | A | A | A |
| 120 | A | A | A |
| 125 | A | B | C |
| 126 | A | A | A |
| 129 | A | A | A |
| 130 | A | A | A |
| 131 | A | B | |
| 132 | A | A | A |

Text Example 4

Test for effect as a fungicide 3-1) in-vitro microbicidal activity against *Candida albicans*

*Candida albicans* IFO 1270 which had been incubated on a Sabouraud's glucose agar (SGA) plate medium at 37° C. for 2 hours was suspended in a sterile physiological saline. The number of cells in the resulting suspension was counted using a blood cell hemocytometer, and the cell centration was adjusted to $1\times10^7$ cells/ml with the sterile physiological saline. In this manner, an inoculation cell solution was prepared. This inoculation cell solution (0.1 ml) and 0.1 ml of a dimethyl sulfoxide (DMSO) were added to 9.8 ml of a Sabouraud's glucose broth (SGB), and the mixture was incubated at 37% for 48 hours while being shaken. After the incubation, the turbidity of the culture medium was measured at a wavelength of 650 nm, and the cell growth inhibition ratio was calculated using the following expression. The fungicidal activity was indicated from this inhibition ratio using the following evaluation standard. The test results of the test compounds are shown in Table 4.

Cell growth inhibition ratio $=(1-W/Y)\times100$ (wherein Y represents a turbidity of a culture medium of a DMSO control group, and W represents a turbidity of a culture medium of a test compound group)

Evaluation standard:

| Cell growth inhibition ratio (%) | Fungicidal activity |
|---|---|
| 100 | A |
| 99-85 | B |
| 84-60 | C |
| 59-0 | — (blank) |

TABLE 4

| (Fungicidal Activity) | |
|---|---|
| No. | C. albicans |
| 1 | A |
| 2 | A |
| 4 | A |
| 7 | A |
| 10 | A |
| 15 | A |
| 19 | A |
| 20 | A |
| 24 | A |
| 33 | A |
| 34 | A |
| 36 | A |
| 37 | A |
| 38 | A |
| 39 | A |
| 40 | A |
| 42 | A |
| 43 | A |
| 45 | A |
| 52 | A |
| 53 | A |
| 54 | A |
| 55 | A |
| 57 | A |
| 60 | A |
| 61 | A |
| 62 | A |
| 63 | A |
| 72 | A |
| 75 | A |
| 79 | A |
| 82 | A |

TABLE 4-continued

| (Fungicidal Activity) | |
|---|---|
| No. | C. albicans |
| 85 | A |
| 90 | A |
| 91 | A |
| 93 | A |
| 94 | A |
| 95 | A |
| 96 | A |
| 97 | A |
| 98 | A |
| 99 | A |
| 100 | A |
| 102 | A |
| 103 | A |
| 104 | A |
| 105 | A |
| 107 | A |
| 108 | A |
| 109 | A |
| 110 | A |
| 112 | A |
| 113 | A |
| 114 | A |
| 118 | A |
| 120 | A |
| 125 | A |
| 128 | A |
| 129 | A |
| 130 | A |
| 131 | A |
| 132 | A |

The compounds of the present invention have excellent effects for controlling wood-rot fungi, plant diseases and fungi of humans and animals, and are useful as industrial, agricultural and medical fungicides.

What is claimed is:

1. A hydroxylamine derivatives of formula (I):

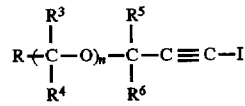

wherein R represents

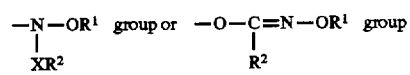

in which $R^1$ and $R^2$ are the same or different and each represents a $C_1$–$C_{12}$ alkyl group; a $C_2$–$C_7$ alkenyl group; a $C_2$–$C_7$ alkynyl group; a $C_3$–$C_7$ cycloalkyl group; a $C_1$–$C_7$ haloalkyl group; a $C_2$–$C_7$ haloalkynyl group; a $C_1$–$C_7$ alkoxy - $C_1$–$C_7$ alkyl group; a phenoxy $C_1$–$C_7$-alkyl group; a phenoxy $C_1$–$C_7$-alkyl group substituted on the ring by one to five substituents which are the same or different and which are selected from a halogen atom, a nitro group, a cyano group, a $C_1$–$C_7$ alkyl group, a $C_1$–$C_7$ haloalkyl group, a $C_1$–$C_7$ alkoxy group, a $C_1$–$C_7$ haloalkoxy group, a $C_1$–$C_7$ alkoxycarbonyl group, a $C_1$–$C_7$ alkylthio group, a $C_1$–$C_7$ haloalkylthio group, a $C_1$–$C_7$ alkylsulfonyl group, a $C_1$–$C_7$ haloalkylsulfonyl group and an amino group substituted by one or two $C_1$–$C_7$ alkyl groups which are the same or different; a $C_1$–$C_7$ alkylthio - $C_1$–$C_7$ alkyl group; a $C_1$–$C_7$ alkylsulfonyl - $C_1$–$C_7$ alkyl group; an amino - $C_1$–$C_7$ alkyl group substituted by one or two substituents which are the same or different and which are selected from a $C_1$–$C_7$ alkyl group and a $C_3$–$C_7$ cycloalkyl group; a phenyl group; a phenyl group substituted on the ring by one to five substituents which are the same or different and which are selected from a halogen atom, a nitro group, a cyano group, a $C_1$–$C_7$ alkyl group, a $C_1$–$C_7$ haloalkyl group, a $C_1$–$C_7$ alkoxy group, a $C_1$–$C_7$ haloalkoxy group, a $C_1$–$C_7$ alkoxycarbonyl group, a $C_1$–$C_7$ alkylthio group, a $C_1$–$C_7$ haloalkylthio group, a $C_1$–$C_7$ alkylsulfonyl group, a $C_1$–$C_7$ haloalkylsulfonyl group and an amino group substituted by one or two $C_1$–$C_7$ alkyl groups which are the same or different a benzyl group; a benzyl group substituted on the ring by one to five substituents which are the same or different and which are selected from a halogen atom, a nitro group, a cyano group, a $C_1$–$C_7$ alkyl group, a $C_1$–$C_7$ haloalkyl group, a $C_1$–$C_7$ alkoxy group, a $C_1$–$C_7$ haloalkoxy group, a $C_1$–$C_7$ alkoxycarbonyl group, a $C_1$–$C_7$ alkylthio group, a $C_1$–$C_7$ haloalkylthio group, a $C_1$–$C_7$ alkylsulfonyl group, a $C_1$–$C_7$ haloalkylsulfonyl group and an amino group substituted by one or two $C_1$–$C_7$ alkyl groups which are the same or different; a naphthyl group; a naphthyl group substituted on the ring by one to seven substituents which are the same or different and which are selected from a halogen atom, a nitro group, a cyano group, a $C_1$–$C_7$ alkyl group, a $C_1$–$C_7$ haloalkyl group, a $C_1$–$C_7$ alkoxy group, a $C_1$–$C_7$ haloalkoxy group, a $C_1$–$C_7$ alkoxycarbonyl group, a $C_1$–$C_7$ alkylthio group, a $C_1$–$C_7$ haloalkylthio group, a $C_1$–$C_7$ alkylsulfonyl group, a $C_1$–$C_7$ haloalkylsulfonyl group and an amino group substituted by one or two $C_1$–$C_7$ alkyl groups which are the same or different; a phenethyl group; a phenethyl group substituted on the ring by one to five substituents which are the same or different and which are selected from a halogen atom, a nitro group, a cyano group, a $C_1$–$C_7$ alkyl group, a $C_1$–$C_7$ haloalkyl group, a $C_1$–$C_7$ alkoxy group, a $C_1$–$C_7$ haloalkoxy group, a $C_1$–$C_7$ alkoxycarbonyl group, a $C_1$–$C_7$ alkylthio group, a $C_1$–$C_7$ haloalkylthio group, a $C_1$–$C_7$ alkylsulfonyl group, a $C_1$–$C_7$ haloalkylsulfonyl group and an amino group substituted by one or two $C_1$–$C_7$ alkyl groups which are the same or different; a cinnamyl group; a cinnamyl group substituted on the ring by one to five substituents which are the same or different and which are selected from a halogen atom, a nitro group, a cyano group, a $C_1$–$C_7$ alkyl group, a $C_1$–$C_7$ haloalkyl group, a $C_1$–$C_7$ alkoxy group, a $C_1$–$C_7$ haloalkoxy group, a $C_1$–$C_7$ alkoxycarbonyl group, a $C_1$–$C_7$ alkylthio group, a $C_1$–$C_7$ haloalkylthio group, a $C_1$–$C_7$ alkylsulfonyl group, a $C_1$–$C_7$ haloalkylsulfonyl group and an amino group having one or two substituents from $C_1$–$C_7$ alkyl groups which are the same or different; a pyridyl group; a pyridyl group substituted on the ring by one to four substituents which are the same or different and which are selected from a halogen atom, a cyano group, a $C_1$–$C_7$ alkyl group, a $C_1$–$C_7$ haloalkyl group, a $C_1$–$C_7$ alkoxy group, a $C_1$–$C_7$ haloalkoxy group, a $C_1$–$C_7$ alkoxycarbonyl group, $C_1$–$C_7$ alkylthio group, a $C_1$–$C_7$ haloalkylthio group, a $C_1$–$C_7$ alkylsulfonyl group, a $C_1$–$C_7$ haloalkylsulfonyl group and an amino group substituted by one or two $C_1$–$C_7$ alkyl groups which are the same or different; a furyl group; a furyl group substituted by one to three substituents which are the same or different and which are selected from a halogen atom, a nitro group, a cyano group and a $C_1$–$C_7$ alkyl group; a thienyl group; or a thienyl group substituted by one to three substituents which are the same or different and which are selected from a halogen atom, a nitro group, a cyano group, and a $C_1$–$C_7$ alkyl group, and X represents $CO_2$, CO or $SO_2$, $R^3$, $R^4$, $R^5$ and $R^6$ are the same or different and each represents a hydrogen atom or a $C_1$–$C_7$ alkyl group, and n represents 0 or an integer of 1.

2. A hydroxylamine derivative as claimed in claim 1, wherein, R represents

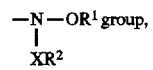

in which $R^1$ and $R^2$ are the same or different and each represents a $C_1$–$C_{12}$ alkyl group; a $C_2$–$C_7$ alkenyl group; a $C_2$–$C_7$ alkynyl group; a $C_3$–$C_7$ cycloalkyl group; a $C_1$–$C_7$ haloalkyl group; a $C_2$–$C_7$ haloalkynyl group; a $C_1$–$C_7$ alkoxy - $C_1$–$C_7$ alkyl group; a phenoxy $C_1$–$C_7$-alkyl group; a phenoxy $C_1$–$C_7$-alkyl group substituted on the ring by one to five substituents which are the same or different and which are selected from a halogen atom, a nitro group, a cyano group, a $C_1$–$C_7$ alkyl group, a $C_1$–$C_7$ haloalkyl group, a $C_1$–$C_7$ alkoxy group, a $C_1$–$C_7$ haloalkoxy group, a $C_1$–$C_7$ alkoxycarbonyl group, a $C_1$–$C_7$ alkylthio group, a $C_1$–$C_7$ haloalkylthio group, a $C_1$–$C_7$ alkylsulfonyl group, a $C_1$–$C_7$ haloalkylsulfonyl group and an amino group substituted by one or two $C_1$–$C_7$ alkyl groups which are same or different; a $C_1$–$C_7$ alkylthio - $C_1$–$C_7$ alkyl group; a $C_1$–$C_7$ alkylsulfonyl - $C_1$–$C_7$ alkyl group; an amino - $C_1$–$C_7$ alkyl group substituted by one or two substituents which are the same or different and which are selected from a $C_1$–$C_7$ alkyl group and a $C_3$–$C_7$ cycloalkyl group; a phenyl group; a phenyl group substituted on the ring by one to five substituents which are the same or different and which are selected from a halogen atom, a nitro group, a cyano group, a $C_1$–$C_7$ alkyl group, a $C_1$–$C_7$ haloalkyl group, a $C_1$–$C_7$ alkoxy group, a $C_1$–$C_7$ haloalkoxy group, a $C_1$–$C_7$ alkoxycarbonyl group, a $C_1$–$C_7$ alkylthio group, a $C_1$–$C_7$ haloalkylthio group, a $C_1$–$C_7$ alkylsulfonyl group, a $C_1$–$C_7$ haloalkylsulfonyl group and an amino group substituted by one or two $C_1$–$C_7$ alkyl groups which are the same or different; a benzyl group; a benzyl group substituted on the ring by one to five substituents which are the same or different and which are selected from a halogen atom, a nitro group, a cyano group, a $C_1$–$C_7$ alkyl group, a $C_1$–$C_7$ haloalkyl group, a $C_1$–$C_7$ alkoxy group, a $C_1$–$C_7$ haloalkoxy group, a $C_1$–$C_7$ alkoxycarbonyl group, a $C_1$–$C_7$ alkylthio group, a $C_1$–$C_7$ haloalkylthio group, a $C_1$–$C_7$ alkylsulfonyl group, a $C_1$–$C_7$ haloalkylsulfonyl group and an amino group substituted by one or two $C_1$–$C_7$ alkyl groups which are the same or different; a naphthyl group; a naphthyl group substituted on the ring by one to seven substituents which are the same or different and which are selected from a halogen atom, a nitro group, a cyano group, a $C_1$–$C_7$ alkyl group, a $C_1$–$C_7$ haloalkyl group, a $C_1$–$C_7$ alkoxy group, a $C_1$–$C_7$ haloalkoxy group, a $C_1$–$C_7$ alkoxycarbonyl group, a $C_1$–$C_7$ alkylthio group, a $C_1$–$C_7$ haloalkylthio group, a $C_1$–$C_7$ alkylsulfonyl group, a $C_1$–$C_7$ haloalkylsulfonyl group and an amino group substituted by one or two $C_1$–$C_7$ alkyl groups which are the same or different; a phenethyl group; a phenethyl group substituted on the ring by one to five substituents which are the same or different and which are selected from a halogen atom, a nitro group, a cyano group, a $C_1$–$C_7$ alkyl group, a $C_1$–$C_7$ haloalkyl group, a $C_1$–$C_7$ alkoxy group, a $C_1$–$C_7$ haloalkoxy group, a $C_1$–$C_7$ alkoxycarbonyl group, a $C_1$–$C_7$ alkylthio group, a $C_1$–$C_7$ haloalkylthio group, a $C_1$–$C_7$ alkylsulfonyl group, a $C_1$–$C_7$ haloalkylsulfonyl group and an amino group substituted by one or two $C_1$–$C_7$ alkyl groups which are the same or different; a cinnamyl group; a cynnamyl group substituted on the ring by one to five substituents which are the same or different and which are selected from a halogen atom, a nitro group, a cyano group, a $C_1$–$C_7$ alkyl group, a $C_1$–$C_7$ haloalkyl group, a $C_1$–$C_7$ alkoxy group, a $C_1$–$C_7$ haloalkoxy group, a $C_1$–$C_7$ alkoxycarbonyl group, a $C_1$–$C_7$ alkylthio group, a $C_1$–$C_7$ haloalkylthio group, a $C_1$–$C_7$ alkylsulfonyl group, a $C_1$–$C_7$ haloalkylsulfonyl group and an amino group substituted by one or two $C_1$–$C_7$ alkyl groups which are the same or different; a pyridyl group; a pyridyl group substituted on the ring by one to four substituents which are the same or different and which are selected from a halogen atom, a cyano group, a $C_1$–$C_7$ alkyl group, a $C_1$–$C_7$ haloalkyl group, a $C_1$–$C_7$ alkoxy group, a $C_1$–$C_7$ haloalkoxy group, a $C_1$–$C_7$ alkoxycarbonyl group, a $C_1$–$C_7$ alkylthio group, a $C_1$–$C_7$ haloalkylthio group, a $C_1$–$C_7$ alkylsulfonyl group, a $C_1$–$C_7$ haloalkylsulfonyl group and an amino group substituted by one or two $C_1$–$C_7$ alkyl groups which are the same or different; a furyl group; a furyl group substituted by one to three substituents which are the same or different and which are selected from a halogen atom, a nitro group, a cyano group, and a $C_1$–$C_7$ alkyl group; a thienyl group; or a thienyl group substituted by one to three substituents which are the same or different and which are selected from a halogen atom, a nitro group, a cyano group, and a $C_1$–$C_7$ alkyl group, and X represents $CO_2$, CO or $SO_2$, $R^3$, $R^4$, $R^5$ and $R^6$ are the same or different and each represents a hydrogen atom or a $C_1$–$C_7$ alkyl group, and n represents 0 or an integer of 1.

3. A hydroxylamine derivative as claimed in claim 2, wherein, $R^1$ represents a $C_1$–$C_7$ alkyl group and $R^2$ represents a $C_1$–$C_7$ alkyl group, a phenyl group, a phenyl group substituted on the ring by one to five substituents which are the same or different and which are selected from a halogen atom, a nitro group, a cyano group, a $C_1$–$C_7$ alkyl group, a $C_1$–$C_7$ haloalkyl group, a $C_1$–$C_7$ alkoxy group, a $C_1$–$C_7$ haloalkoxy group, a $C_1$–$C_7$ alkoxycarbonyl group, a $C_1$–$C_7$ alkylthio group, a $C_1$–$C_7$ haloalkylthio group, a $C_1$–$C_7$ alkylsulfonyl group and a $C_1$–$C_7$ haloalkylsulfonyl group, a benzyl group, a benzyl substituted on the ring by one to five substituents which are the same or different and which are selected from a halogen atom, a nitro group, a cyano group, a $C_1$–$C_7$ alkyl group, a $C_1$–$C_7$ haloalkyl group, a $C_1$–$C_7$ alkoxy group, a $C_1$–$C_7$ haloalkoxy group, a $C_1$–$C_7$ alkylthio group, a $C_1$–$C_7$ haloalkylthio group, a $C_1$–$C_7$ alkylsulfonyl group and a $C_1$–$C_7$ haloalkylsulfonyl group, X represents $CO_2$ or CO, $R^3$, $R^4$, $R^5$ and $R^6$ are the same or different and each represents a hydrogen atom or a $C_1$–$C_7$ alkyl group, and n represents 0 or an integer of 1.

4. An industrial fungicidal composition comprising an effective amount of a hydroxylamine derivative as claimed in claim 1.

5. An agricultural and horticultural fungicidal composition comprising an effective amount of a hydroxylamine derivative as claimed in claim 1.

6. A medical fungicidal composition comprising an effective amount of a hydroxylamine derivative as claimed in claim 1.

* * * * *

UNITED STATES PATENT AND TRADEMARK OFFICE
CERTIFICATE OF CORRECTION

PATENT NO. : 5,733,935
DATED : March 31, 1998
INVENTOR(S) : Nobuharu ANDOH, Tsutomu NISHIGUCHI, and Katsutoshi ENDO It is certified that error appears in the above-identified patent and that said Letters Patent is hereby corrected as shown below:

Title page, in item [56], "References Cited", insert:

--FOREIGN PATENT DOCUMENTS--

```
--47-43829       11/1972      Japan--
--55-36498       03/1980      Japan--.
```

Signed and Sealed this

Fifteenth Day of September, 1998

Attest:

BRUCE LEHMAN

*Attesting Officer*     *Commissioner of Patents and Trademarks*

Disclaimer 5,733,935 - Nobuharu Andoh, Osaka; Tsutomu Nishiguchi; Katsutoshi Endo, both of Kawachinagano, all of Japan. HYDROXY-LAMINE DERIVATIVES AND FUNGICIDES CONTAINING THE SAME. Patent dated March 31, 1998. Disclaimer filed April 21, 1999, by the assignee, Nihon Nohyaku Co., Ltd.

Hereby enters this disclaimer to the entire term of said patent.
*(Official Gazette,* June 1, 1999)